United States Patent [19]

Nilsson

[11] Patent Number: 5,936,075
[45] Date of Patent: Aug. 10, 1999

[54] AMINO-DEOXY-DISACCHARIDES AND AMINO-DEOXY-OLIGOSACCHARIDES

[75] Inventor: Kurt G. I. Nilsson, Lund, Sweden

[73] Assignee: Bioflexin AB, Lund, Sweden

[21] Appl. No.: 08/474,173

[22] Filed: Jun. 7, 1995

Related U.S. Application Data

[63] Continuation of application No. PCT/SE94/00461, May 17, 1994.

[51] Int. Cl.⁶ .............................. C07H 15/00; C07H 17/00
[52] U.S. Cl. ......................... 536/17.5; 536/4.1; 536/17.2
[58] Field of Search ................................... 536/4.1, 17.2, 536/17.5

[56] References Cited

U.S. PATENT DOCUMENTS

| | | | |
|---|---|---|---|
| 4,415,665 | 11/1983 | Mosbach et al. | 435/179 |
| 4,918,009 | 4/1990 | Nilsson | 435/73 |
| 5,246,840 | 9/1993 | Nilsson | 435/101 |
| 5,372,937 | 12/1994 | Nilsson | 435/74 |
| 5,405,752 | 4/1995 | Nilsson | 435/7.94 |
| 5,532,147 | 7/1996 | Nilsson | 435/100 |
| 5,599,694 | 2/1997 | Nilsson | 435/94 |

FOREIGN PATENT DOCUMENTS

| | | |
|---|---|---|
| 516155 | 12/1992 | European Pat. Off. . |
| 3-284690 | 12/1991 | Japan . |
| 92/22565 | 12/1992 | WIPO . |

*Primary Examiner*—Kathleen K. Fonda
*Attorney, Agent, or Firm*—Smith, Gambrell & Russell, LLP; Beveridge, DeGrandi, Weilacher & Young Intellectual Property Group

[57] ABSTRACT

Synthesis of an amino-disaccharide, amino-oligosaccharide or a derivative thereof, characterized in that a monosaccharide, a disaccharide, an oligosaccharide, a glycoside or a derivative thereof, in the presence of a glycosidase as catalyst, is reacted with an amino-deoxy-saccharide or a derivative thereof, and that the amino-saccharide is isolated from the product mixture directly or after chemical/enzymatic modification.

1 Claim, No Drawings

AMINO-DEOXY-DISACCHARIDES AND AMINO-DEOXY-OLIGOSACCHARIDES

REFERENCE TO A RELATED APPLICATION

This is a continuation of international application PCT/SE94/00461, filed May 17, 1994, which designated the United States, and which is incorporated by reference in its entirety.

INTRODUCTION AND BACKGROUND

The present invention describes a new method for synthesis of an amino-deoxy-disaccharide or an amino-deoxy-oligosaccharide.

It has been found that the oligosaccharide part of various glycoconjugates (especially glycolipids and glycoproteins) have a number of important functions in vivo (Biology of Carbohydrates, vol. 2, Ginsburg et al., Wiley, N.Y., 1984; The Glycoconjugates, vol. I–V, Academic Press, New York; S. Hakomori, Ann. Rev. Biochem., vol 50, pp. 733–64; Feizi, Nature, pp 314, 1985; S. Hakomori, Chemistry and Physics of Lipids, vol. 42, pages 209–33). Among other thing it was found that the carbohydrate structures are important for the stability, activity, localization, immunogenicity and degradation of glycoproteins;

carbohydrates are antigenic determinants (for example blood group antigens);

carbohydrates function as receptors when bound to cell surfaces for pathogens, proteins, hormones, toxins and during cell—cell interactions;

carbohydrates are important for oncogenesis, since specific oligosaccharides have been found to be cancer-associated antigenic determinants;

frequently, only a smaller sequence (di- or trisaccharide) of the carbohydrate part of the glycoconjugate is required for full biological activity (e.g. receptor activity).

Universities and industry are at present working intensely on developing the use of biologically active oligosaccharides within a number of different fields, such as novel diagnostics and blood typing reagents;

highly specific materials for affinity chromatography;

cell specific agglutination reagents;

targetting of drugs;

monoclonal antibodies, specific against e.g. cancer-associated reagents;

therapy;

development of a new type of therapy, as an alternative to antibiotics, based on the inhibition of the attachement of bacteria and virus on cell surfaces with specific oligosaccharides;

stimulation of the growth of plants and protection against pathogens.

Besides the above mentioned areas, a considerable future market is envisaged for fine chemicals based on biologically active carbohydrates.

Amino-saccharides, where an —OH group in the saccharide is exchanged for an —$NH_2$ group, in several cases have a higher (or modified) biological activity than the corresponding hydroxyl- or N-acetylamino-deoxy-saccharides, e.g. in the binding to selectins important for the initiation of inflammation processes (binding of leucocytes to epithelial cells in blood vessels). The opportunity to use such saccharides therapeutically, e.g. in acute or chronic inflammatory conditions (e.g. reperfusion, injury, and septic shock) is investigated. An important component in this and in other cases is the selective synthesis of di- and oligosaccharides in sufficient quantities. The present invention describes a novel technique for synthesis of amino-saccharides.

Amino-deoxy-di-, tri- or higher oligosaccharides which contain one or more amino —$NH_2$ groups are of high interest for food, agricultural, pharmaceutical or diagnostic applications of carbohydrates, to modify the metabolism of the substance and/or to increase the biological effect of the natural substance.

About ten different monosaccharides are included in the carbohydrate part of the glycoconjugates: D-glucose (Glc), D-galactose (Gal), N-acetyl-D-glucosamine (GlcNAc), N-acetyl-D-neuraminic acid (Neu5Ac), D-mannose (Man), L-fucose (Fuc), N-acetyl-D-galactosamine (GalNAc), xylose (Xyl), and arabinose (Ara) (the abbreviations in brackets are according to IUPAC-IUB's abridged terminology for monosaccharides, J.Biol.Chem. (1982), vol. 257, pages 3347–3354, in which publication one also can find the nomenclature used in this text to describe oligosaccharide sequences). The number of possible structures will be almost infinitely great because both the anomeric configuration and the position of the O-glycosidic bond can be varied.

The organic chemical techniques used today for synthesis of these oligosaccharide structures require an extensive protective group chemistry with many steps of synthesis and expensive catalysts (see e.g. Binkley: Modern Carbohydrate Chemistry, Marcel Dekker, New York, 1988, with references). Low total yields are obtained in these complicated reaction schemes and the technique is not favorable, especially for larger scale work.

Selective chemical synthesis of amino group containing carbohydrates and derivatives require advanced protection group chemistry with many synthetic steps. (see e.g. Binkley: Modern Carbohydrate Chemistry, Marcel Dekker, New York, 1988, with references). Efficient techniques for preparation of such carbohydrates and derivatives thereof are thus desired.

The present invention describes a process which makes possible a drastically simplified synthesis of derivatised or unmodified di-, tri-, and higher oligosaccharides which contain at least one —$NH_2$ (amino) group. Carbohydrate amino derivatives which required several reaction steps to synthesis with previous methods, can, with the method according to the present invention, now be obtained with only one reaction step and with absolute stereospecificity.

Enzymes are nature's own catalysts with many attractive characteristics, such as higer stereo-, regio-, and substrate selectivity as well as high catalytic activity under mild conditions. Today, great hopes are therefore placed in being able to utilize enzymes for large-scale selective synthesis of oligosaccharides with fewer reaction steps and consequently higher total yields than by organic chemical methodology.

Both hydrolases (glycosidases, EC 3.2) and glycosyltranferases (EC 2.4) can be used for synthesis (glycosidases: see Nisizawa et al, in "The Carbohydrates, Chemistry and Biochemistry", 2nd Ed., vol. IIA, pages 242–290, Academic Press, New York, 1970). With glycosidases, reversed hydrolysis (equilibrium reaction) or tranglycosylation (kinetic reaction) are often used to obtain synthesis (see e.g. K. G. I. Nilsson, Carbohydr. Res. (1987), vol. 167, pages 95–103; Trends in Biochemistry (1988), vol. 6, pages 256–264).

Reversed hydrolsis: 

Transglycosylation:
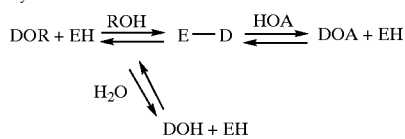

(DOH is donor saccharide, DOR is donor glycoside with α- or β-glycosidically bound aglycon (—R), HOA is acceptor saccharide and EH is enzyme).

With transferases, a nucleotide sugar (non-limiting examples are UDP-Gal, CMP-Sia, UDP-GalNAc, GDP-Fuc, etc), which is relatively expensive, is used as donor. Furthermore, glycosidases are abundant and can often be used directly without purification.

The synthetic method according to the invention includes at least one process characterized by that a glycosidase (EC 3.2) is used to catalyze an equilibrium or a transglycosylation reaction between an acceptor substance, which consists of a mono-, di-, tri- or higher oligosaccharide which contains at least one amino-deoxy-group

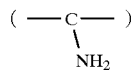

and which is modified or unmodified, and a glycosyl donor, which is a monsaccharide, disaccharide, oligosaccharide or a glycoside or derivative thereof, and that the product is used for continued synthesis and/or is isolated from the product mixture.

In this way one obtains, according to the invention, stereospecific synthesis of di-, tri-, or higher amino-deoxy-oligosaccharides or derivatives thereof, which can be used directly, or after further synthesis, for a number of various applications, e.g. for pharmaceutical/medical/diagnostical studies, for applications in therapy or diagnostics, as additives in cosmetics or in food, for modification of separation material, affinity chromatography, modification of amino acids, peptides, proteins, fatty acids, lipids, enzymes, or recombinant proteins.

In the synthesis according to the invention, the capacity of glycosidases to form stereospecific glycosidic linkages between a glycosyl donor (DR in the scheme below, where D symbolizes the transferred carbohydrate part) and a glycosyl acceptor (HOA), summarized in the scheme below:

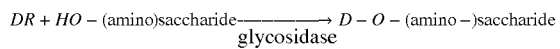

The reaction according to the invention can be carried out according to two principles, either with equilibrium controlled synthesis (R=H), or with transglycosylation reaction (R=F, or an organic group; kinetically controlled reaction). These general types of reactions are well know to the expert and their carrying out, as well as the choice of glycosyl donor and glycosidase, do not restrict the scope of the invention.

SUMMARY OF THE INVENTION

Synthesis of an amino-disaccharide, amino-oligosaccharide or a derivative thereof, characterized in that a monosaccharide, a disaccharide, an oligosaccharide, a glycoside or a derivative thereof, in the presence of a glycosidase as catalyst, is reacted with an amino-deoxy-saccharide or a derivative thereof, and that the amino-saccharide is isolated from the product mixture directly or after chemical/enzymatic modification.

DETAILED DESCRIPTION OF THE INVENTION

The synthesis, according to the invention, is carried out by reacting a monosaccharide, a disaccharide, an oligosaccharide, a glycoside or a derivative thereof with an amino-deoxy-saccharide or a derivative thereof in the presence of a glycosidase (EC 3.2) as a catalyst.

As nonlimiting examples of amino-deoxy-monosaccharides which can be used as acceptors one can mention a 2-amino-2-deoxy-glucopyranoside, a 2-amino-2-deoxy-galactopyranoside, or a 2-amino-2-deoxy-mannopyranoside (thus, in the scheme below, $R_3$, $R_4$ and $R_6$ are —OH and $R_1$ is one of e.g. pentenyl-, —SEt, —SPh, —OEtBr, —OEtSiMe$_3$, —OAll, —OPh, —OCH$_2$Ph, or —OR, where R is e.g. CH$_3$(CH$_2$)n; n is an integer, preferably in the range 0–12; or where R is for example an amino acid residue, peptide residue, or a derivative thereof):

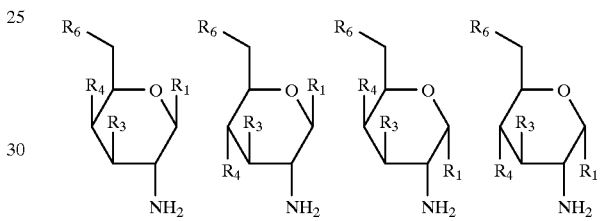

Other nonlimiting examples of amino-deoxy-saccharides is an 2, 3, 4, 5 or 6 amino-monosaccharide as above, which has been derivatised in one or two of the positions 2, 3, 4, 5 or 6. As examples of such derivatives one can mention derivatives in which one or two of the hydroxyl groups have been modified to an allyloxy- (CH$_2$=CH—CH$_2$O—), bensyloxy- (PhCH$_2$O—), bensoyloxy-(PhCOO—), chloroacetyloxy-(ClCH$_2$COO), p-methoxybensyloxy-(p-MeO-PhCH$_2$O—), trityl- (Ph$_3$CO—), trialkylsilyloxy-, tosylate-, mesylate-, phosphate-, sulfate-, carboxylate, esters such as RCOO— where R is CH$_3$(CH$_2$)n (n=1–20) or a pivaloyloxy-group or derivatives in which two vicinal hydroxyl groups have been modified e.g. bensylidene acetal, isopropylidene ketal or an ortho ester, pivaloyl-group, tetrahydropyranyl, (2-methoxyethoxy) methylisopropylidene ketal, cyclohexylidene ketal, benzylidene acetal, orthoester, —ONO$_3$, derivative of sulfate-, phosphate-, carboxylate, esters i.e. of the type —OC(O)R as acetyl-, butanoyl-, octanoyl-, benzoyl-, pivaloyl-, etc. The structures below, modified in a similar way, can also be used as acceptor substances in the method according to the invention.

If modified amino monosaccharide is used, the choice of the type of modification of the acceptor is decided by what is desired in the specific situation and the literature is rich in information on protection groups/modification of carbohydrates and carbohydrate synthesis in general (e.g. "Modern Carbohydrate Chemistry", Binkley, Marcel Dekker, 1988 with references; Paulsen, Chem. Soc. Rev., vol. 13, pages 15–45). Below are a few examples of acceptor substance categories which can be used according to the invention but which in no way are meant to restrict the scope of the invention.

Similarly, modified amino di, tri- or higher oligosaccharides can also be used as acceptors.
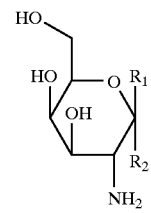
I
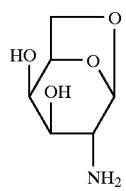
V
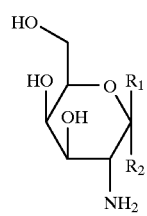
II
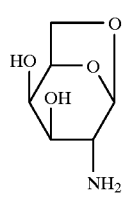
VIII
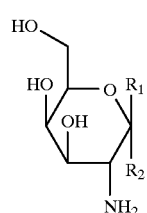
III
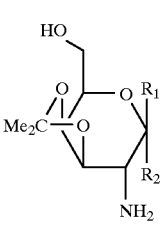
VI
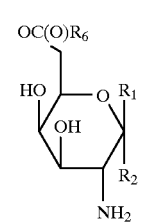
II
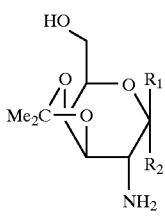
X
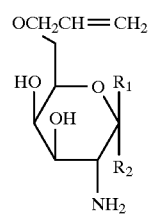
III
R₁ OR R₂ = H
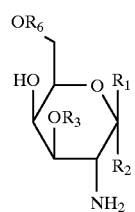
VII
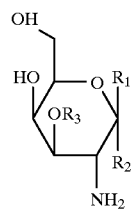
IV
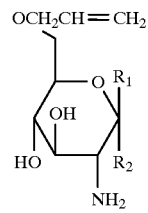
VIII
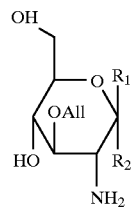
XI
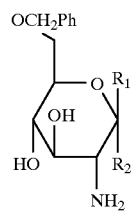
IX -continued

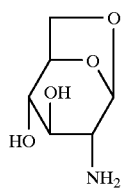
X

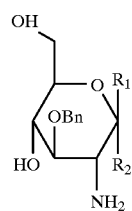
XII

In the structures I–XI above, $R_3$ is for example an alkyl, allyl, benzyl, chlorobensyl, benzoyl-group or another type of suitable protection group for the specific synthesis. $R_6$ can be aromatic group such as Ph- or an alkyl group (e.g. propyl- or $(CH_3)_3$-group). In the structures XII–XVII, $R_3$ is for example an acetyl-, phenoxyacetyl-, methoxyacetyl- or an chlorometoxyacetyl group. $R_6$ can be an aromatic group, such as Ph- or an alkyl group (e.g. propyl- or $(CH_3)_3$ group). If $R_2$ for example is H, then $R_1$ is one of the groups which has been mentioned for $R_1$ above, and vice versa if $R_1$ instead is H. Similarly, position 4 can be modified instead of position 3 or 6 in the examples above, and other positions than the 2 position may be modified with an amino-deoxy group.

As an example to illustrate the invention, but which in no way is meant to limit the scope of the invention, can be mentioned that if, for example, α-galactosidase is used as enzyme and 2-amino-2-deoxy α-D-galactopyranoside is used as acceptor substance, and if, for example raffinose, methyl α-D-galactopyranoside, GalαF (F=fluoro) (or p-nitrophenyl) α-D-galactopyranoside is used as glycosyl donor (transglycosylation reaction), an α-glycosidically linked 2-amino-2-deoxy-digalatosyl derivative of the type

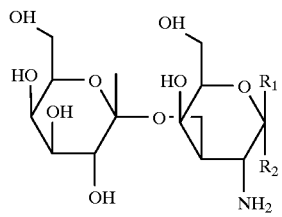

i.e. a 2-$NH_2$-2-deoxy-derivative of Galα1-3Galα-R, is obtained. As another example, if I is used as acceptor and a α-galactosaminidase, and e.g. (GalNAcα-OPh, GalNAcαF or GalNAcα-OPhNo$_2$-p, is used as glycosyl donor, a 2-O-derivative of GalNAcα1-3Galα-R is obtained.

The products can be used if desired for further synthesis, e.g. of higher oligosaccharide with chemical synthesis and the literature is extensive on how to use such partially protected carbohydrates (see references in Binkley and Paulsen mentioned above).

If a β-galactosidase is used instead of an α-galactosidase and if lactose, or for example p-nitrophenyl-β-D-galactopyranoside, is used as glycosyl donor, and if 2-amino-2-deoxy-glucose or a derivative thereof (see e.g.

XII–XVII above) is used as acceptor, β-bound derivatives of Gal-GlcNH$_2$ or Gal-GlcNH$_2$—R are obtained. Examples of partially protected Gal-GlcNH$_2$ or Gal-GlcNH$_2$—R derivatives, which can be used e.g. for synthesis of Lewis-x or Lewis-a trisaccharide structures (or which can be used for further synthesis of disaccharide derivatives of these) are given below:

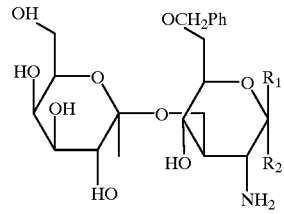

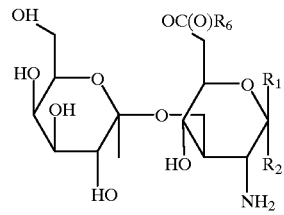

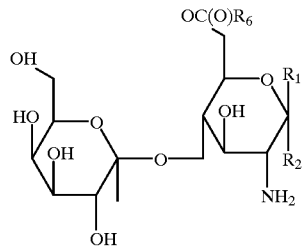

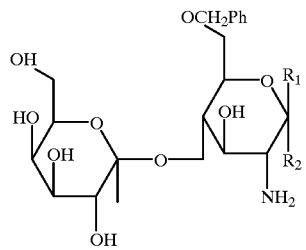

Moreover, if instead an α-L-fucosidase is used with, for example, nitrophenyl α-L-fucopyranoside or with Fucα-F as glycosyl donor, one can synthesis the corresponding derivatives of e.g. α-bound Fuc-Gal-NH$_2$—R and of α-bound Fuc-GlcNH$_2$—R with the method according to the invention, similarly with N-acetyl-β-glucosaminidase or N-acetyl-β-galactosaminidase one can prepare derivatives of β-bound GlcNAc-Gal-NH$_2$ and GlcNAc-GlcNH$_2$ or GalNAc-Gal-NH$_2$ and GalNAc-GlcNH$_2$, respectively, with β-glycosides of GlcNAc and GalNAc, respectively, as glycosyl donors. Similarly, α-sialidase can be used to catalyze synthesis of e.g. sialylated 2-amino-2-deoxy-galactose (Neu5Acα-GalNH$_2$) or of 2-amino-2-deoxy-galactosamine-derivatives (derivatives of Neu5Acα-GalNH$_2$) by employing e.g. nitrophenyl glycoside of N-acetylneuraminic acid and a partially protected 2-amino-2-deoxy-galactose derivative, respectively, as acceptor.

If an endoglycosidase is used, one can prepare longer oligosaccharide derivatives with the method according to the invention. Then, the donor substance is of the type disaccharide, tri- or higher oligosaccharide or a glycoside, e.g. nitrophenyl glycoside of any of these. Similarly, any of the R groups of the acceptor substance might be a saccharide unit.

The reaction above can also be carried out as equilibrium reactions with monosaccharides as glycosyl donors.

The benzyl- or the allyl group (or other groups mentioned in connection with the figures above) in the products above, can easily be chemically changed by the expert to a wide range of groups, and in this way selective synthesis of different amino-deoxy-disaccharide derivatives (e.g. O-phosphate, O-sulfate, etc) or higher amino-deoxy-oligosaccharides can be selectively synthesized according to the invention.

The substrates are selected with regard to the oligosaccharide which is to be synthesized, and are often commercially available or can by synthesized by organic or enzymatic methods and therefore do not restrict the use of the invention. The donor substrates which are used according to the invention are of the same type which have been used in previous transglycosylation reactions (see for example the articles by K. G. I. Nilsson in Carbohydrate Res. vol. 167 and in Trends in Biotechnology, vol. 6 as noted above).

As further examples of acceptor substances which can be used with the method according to the invention can be mentioned amino-deoxy di- or oligosaccharides (or glycosides thereof) in which the carbohydrate part contains one or more of the following monosaccharides: D-glucose, D-galactose, D-mannose, N-acetyl-neuraminic acid, N-acetyl-D-galactosamine, N-acetyl-D-glucosamine and L-fucose, or analogs of these. When the acceptor substance is a glycoside, the aglycone can be a glycosidically bound ($\alpha$- or $\beta$-configuration) aliphatic or aromatic compound (as for example methyl, ethyl, 2-bromoethyl, $(CH_2)_n COOMe$, n>1, allyl or other substances that can be polymerized, benzyl, pentenyl, trimethylsilylethyl, amino acids, derivatives thereof, peptides, derivatives thereof, nitrophenyl, etc).

Other types of aglycons of special interest are amino acids (serine, threonine, hydroxyproline, hydroxylysine, asparagine, etc), peptides, lipids and derivatives or analogs to substances within these three groups. The amino acid and peptide glycosides can be protected on their amino and/or carboxyl groups with the common protecting groups used in peptide synthesis (FMOC, CBZ, BOC, etc). By using usch aglycones fragments or analogs of glycoconjugates can be synthesized according to the invention; the terms aglycones, fragments and analogs are terms well known to those skilled in the art. Moveover, the aglycon can be an amino, nitrile, or an amido group or a fluorogenic substance, or may contain a phosphate, sulfate, or carboxyl group or a derivative thereof. Another important type of amino-deoxy saccharide derivatives consists of substances where the ring oxygen (i.e. the C-5 oxygen of hexoses), has been replaced by sulfur, nitrogen, etc. The glucose analog moranoline, where the C-5 oxygen has been replaced by nitrogen, is an example of such a derivative. Oligosaccharide analogs that are efficient inhibitors against enzymes or carbohydrate binding proteins may in this manner be synthesized according to the invention.

The donor substances which can be used with the method according to the invention are the same as those employed in previous methods involving enzymatic transglycosylations (see references above) and thus do not limit the scope of the invention.

As examples of donor substances that can be used with the method according to the invention may be mentioned monosaccharide glycosides and di- or oligosaccharides (or gylcosides thereof) in which the carbohydrate part contains one or more of the monosaccharides D-galactose, D-glucose, D-mannose, N-acetyl-neuraminic acid, N-acetyl-D-galactosamin, N-acetyl-D-glucosamin and L-fucose. As examples of suitable glycosyl donors may be mentioned the nitrophenyl $\alpha$- or $\beta$-glycosides of the monosaccharides above, lactose, dimannose and raffinose. As examples of suitable donor substances for endoglycosidases may be mentioned nitrophenyl derivatives of biologically active carbohydrate sequences (e.g. Gal$\beta$1-3GlcNAc$\beta$-OPhNO$_2$-p), biologically active oligosaccharides or structures of the type Glc($\beta$1-3Glc)$_n\beta$1-3Glc (n>1).

The concentration of the glycosyl donor in the reaction mixture is selected with regard to the oligosaccharide which is to be synthesized and also with regard to the properties of the enzyme and therefore do not restrict the use of the invention. In some cases, addition of the donor in smaller portions may be advantageous in order to minimize the risk that the donor also acts as an acceptor (unless this is desired).

The enzymes are selected primarily with regard to which oligosaccharide is to be synthesized. The enzyme may be used in situ or after partial or complete purification from their natural environment. The enzyme may be used in soluble form or immobilized to a solid support by e.g. adsorption, encapsulation, chelation, precipitation or covalent binding.

Examples of $\alpha$- and $\beta$-glycosidases which may be used according to the invention are D-mannosidases, D-galactosidases, L-fucosidases, N-acetyl-D-galactosaminidases, sialidases, hexosaminidases and other glycosidases of EC group 3.2 (Enzyme Nonmenelature, Academic Press, 1984). Both endo- and exoglycosidases may be used in the method according to the invention.

The degree of purity of the enzyme employed is not critical. The enzyme may be used in situ or after complete or partial isolation from it natural biological environment. Also, a crude extract of the organism or a tissue thereof may be used. The enzyme may also have been obtained after precipitation with e.g. ammonium sulfate. The enzyme may be present in crystalline form or be enclosed within micelles. The biochemical literature is rich in detailed information about the purification and isolation of glycosidases. The enzyme may be produced with recombinant techniques. Then, if desired, one or more of the amino acids in the amino acid sequence of the enzyme may be changed in order to optimize the properties of the enzyme, e.g. themostability, catalytic efficiency and/or regioselectivity.

The enzyme may be used in soluble form or may be immobilized by e.g. adsorption, encapsulation, chelation, precipitation or covalent binding to a solid support, such as a polymeric substance, or a derivative thereof which is insoluble in protic or aprotic solvents (Methods in Enzymology, vol. 44, Academic Press, 1976). The form selected is not critical to the invention. If the enzyme is used in soluble form, it may first have been chemically modified in a suitable manner in order to e.g. increase the thermostability or the stability in organic cosolvents. Enzyme immobilized to an insoluble polymer comprising, for example, agarose, cellulose, hydroxyethyl acrylate, glass, silica, polyacrylic amide, polyacrylate-based plastics, etc., is readily separated from the product mixture, and the enzyme may thus be reused. An additional advantage is that in many cases a certain stabilization against elevated temperatures and organic cosolvents is obtained.

Moreover, the products can be used for further enzymatic synthesis with glycosidases or glycosyltranferases. For example, $\alpha$-sialyltranserase can be used to catalyze the formation of sialylated Gal-GlcNAc-derivatives and $\beta$-galactosyltransferase can be used to form oligosaccharide derivatives of the type Gal-GlcNAc-Gal-R, which then can eventually be sialylated and/or be used for further chemical synthesis, etc.

If a modified 2-amino galactoside or glucoside is used as acceptor, the choice of aglycon is made with regard to the application of the product. Aglycons of special interest are amino acids (serine, threonine, hydroxyproline, hydroxylysine, asparagine, etc.) peptides, lipids and derivatives or analogs of substances within these three groups. Amino acid or peptide glycosides can be protected on their amino- and/or carboxyl functions with common groups used in peptide synthesis (FMOC, CBZ, BOC, etc). Product obtained with modified alkyl glycosides (e.g. modified methyl-, octyl-, docecyl glycosides) as acceptor substances, may be used as inhibitors in affinity chromatography or in agglutination tests, inhibition-based therapy or for drug-targeting, as structural units for further enzymatic synthesis. Nitrophenyl glycosides can be reduced to aminophenyl glycosides. Glycosides with a polymerisable aglycon, as for example 2-hydroxyethylmethacrylate, can be used. As an example of a N-glucosidically bonded aglycon, —NHCO $(CH_2)_5NH_2$, may be mentioned. Other types of aglycons which can be used are those used e.g. in the synthesis of glycolipids/analogs for conversion to ceramides/analogs, e.g. aglycons of the type described by Magnusson et al in J. Org. Chem., 1990. Thioglycosides (e.g. SEt or SPh) can be used with the method according to the invention to produce products which are suitable for further chemical synthesis. The choice of protection group/derivative, aglycon, position of derivatized hydroxyl groups, can be used to influence the yield and regioselectivity of the reactions with the method according to the invention. Thus, for example, the use of more hydrophobic aglycons (e.g. p-metoxy-benzyl-, benzyl-, compared with e.g. allyl-) can result in a higher yield at the same acceptor concentration.

The enzymes are selected with regard to the final oligosaccharide which is to be synthesized. The enzyme can be used in situ (especially several glycosidases) or after partial or complete purification from their natural environment. The enzyme may be used in soluble form or immobilized to a solid phase by e.g. adsorption, encapsulation, chelation, precipitation or covalent binding. Simultaneous use of glycosidase and glycosyltransferase in soluble form or immobilized to a solid phase (eventually co-immobilized) may be advantageous according to the invention in facilitating the conversion of the intermediate oligosaccharide product to the final product oligosaccharide. In this way the method according to the invention gives important advantages compared to previous methods: purification of intermediary product is not necessary, secondary hydrolysis is minimized (i.e. higher yield), and trisaccharides or higher oligosaccharides can be synthesized in a minimum of "pots" (in some cases one-pot reactions). This is facilitated by the high acceptor specificity of most glycosyltransferases: the transferase does not react with the wrong isomer.

The synthetic procedure according to the invention can be carried out under highly diverse conditions as regards, for example, pH, type of buffer, temperature and concentration of the reactants. Various cosolvents (N,N-dimethyl formamide, acetonitrile, dimethyl sulfoxide, dioxane, pyridine, methanol, ethanol, ethylene glycol, etc) may be used and in varying concentrations together with water (0–99%). Moreover, the reactions can be carried out in two-phase systems: water-organic solvent. THe use of acceptor aminosaccharides modified with organic groups facilitates recovery of the product in the organic phase.

The reaction conditions are not critical but are selected primarily on the basis of the properties of the reactants employed in the synthesis concerned, and also on the basis of practicality. For example, it may be mentioned that it is usually convenient to use room temperature with enzymes and, in the case of water-rich medium, the pH is usually in the range 4–11. The solubility of amino-saccharides in water is increased/decreased by decreased/increased pH, and in some cases a pH below 8 and above 4 is preferably used to increase the solubility of the acceptor amino-saccharide.

Organic cosolvents may be used to minimize the hydrolytic side-reaction. For the same reason, two-phase systems may be used. Examples of cosolvents are tetrahydrofurane, acetonitrile, DMF. The choice of solvent and of the concentration or organic solvent can easily be made by the expert and does not limit the scope of the invention. Use of high concentrations of organic solvent (up to almost 100% of the total volume solvent) can be especially advantageous when acceptor derivatives with hydrophobic groups which have good solubility in organic solvents are used, e.g. acceptors modified with ester groups (e.g. acetyl-, bensoly-, butanoyl-, pivaloyl-, octanoyl-grupper, etc.) and/or with for example allyl-, bensyl-, trityl- or other groups. In this way relatively high concentration of the acceptor can be achieved in organic solvents and the hydrolytic side-reaction can be decreased due to the low water content. The method according to the invention allows synthesis in organic solvent of e.g. amino deoxy trisaccharde derivatives and higher oligosaccharide derivatives with exoglycosidases by using hydrophobic protected derivatives of amino deoxy di-, tri- or oligosaccharides, which has only one or a few free dydroxyl groups, as acceptors.

To increase the solubility/availability in organic solvent and facilitate the reaction with the donor substance, one can use for example phenyl boronate, which forms a complex with saccharides with vicinal diols and the resulting donor-boronate complex has, because of the phenyl group, a higher solubility in organic solvent.

The reaction temperature may also be varied to influence product yield and the stability of the enzyme and does not restrict the scope of the invention. The temperatures most frequently used lie in the range 4°–55° C., but lower temperatures and temperatures below 0° C. can be used which can be facilitated if organic cosolvent is used. Higher temperatures can be used with thermostable glycosidases and substrates, and also with enzymes stabilized against thermal denaturation by employing, for example, high substrate concentrations (Johansson et al, Biotechnol. Lett. (1986), vol. 8, pages 421–424). An advantage with high temperatures is, for example, that high substrate concentrations may be used, which reduces the water activity and thus increases the yield of product. Another advantage is that the activity of the enzyme increases, which means shorter reaction times at increased temperatures. One additional advantage is that glycosides, e.g. methyl or ethyl glycosides, which are hydrolyzed slowly at room temperature can be used as suitable gylcosyl donors at increased temperatures (50°–60° C.). The upper temperature limit is determined by the thermostability of the enzyme in the reaction medium. For some transglycosidations, a lower temperature was found to give a higher yield of product glycoside.

The concentration of the acceptor is a parameter which can be used to influence the yield of the reactions according to invention. High concentrations are preferrable in both equilibrium and transglycosylation reactions to mimimize hydrolytic side-reactions, which usually means that depending on the solulility of the acceptor, ca 0.05–7 M concentration of acceptor is used. A high concentration of donor is often used and especially in equilibrium reactions. In general, high concentrations of substrates are obtained by heating the reaction mixture to near the boiling point for a few minutes, allowing the solution to cool to the reaction temperature (usually 4°–75° C., depending on the temperature for optimum yield and thermostability of the enzyme/substrate) and then add the enzyme. Cosolvents can be used to increase the solubility of substrates with hydrophobic groups.

The reaction can be monitored by means of TLC, HPLC, or by spectrophotometric measurement of liberated aglycon (e.g. p-nitrophenol, 400 nm). Charring of TLC-plates with ninhydrin may be used for detection of $NH_2$-groups. When a desirable yield of the product has been obtained, the reaction is terminated by denaturation of the enzyme by changing the pH, increasing the temperature and/or adding organic cosolvent (such as ethanol). Heating to 60°–85° C. for 3–5 min (eventually followed by addition of ethanol to a concentration of about 80%) is usually sufficient.

Various techniques may be used for isolation of the product. Precipitation from the water-phase or from an organic solvent (such as e.g. ethanol, methanol, ethyl acetate) is useful, especially when an excess of one of the reactants is used or when the donor, acceptor or products have different solubilities. After the equilibrium controlled synthesis or the transglycosylation reaction and after e.g. heat treatment as above and dilution of the reaction mixture, it can be useful to add a second glycosidase, which has a different regioselectivity than the glycosidase used in the synthesis. In this way, any unwanted regioisomers (for example with 1–6 linkages) may be more or less selectively hydrolyzed, which facilitates isolation of the desired product.

Precipitation, extraction of the water phase with an organic solvent, and hydrolysis of byproducts are complementary to chromatography (ion exchange chromatography, gel filtration, HPLC with, for example, amino-silica, reversed phase silica or the new Dionex columns).

Some examples of how the invnetion can be used in practice, but which by no means are meant to restrict the scope of the invention, are given below.

Examples of substances, which can be used as donor saccharides (DR, where D is the transferred glycosyl group in the reaction) according to the invention is D-glucose, D-mannose, L-fucose, D-galactose, xylose, N-acetyl-D-glucosamine, N-acetyl-D-galactosamine, N-acetyl-neuraminic acid, glycosides of these, disaccharides or oligosaccharides containing one or more of the monosaccharides above (e.g. lactose, raffinose, chitobiose), and derivatives of any of the substances mentioned above, e.g. modified in one or more of the ring hydroxyl groups.

The reaction according to the invention can therefore be summarized as follows:

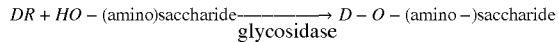

$$DR + HO-(amino)saccharide \xrightarrow{glycosidase} D-O-(amino-)saccharide$$

where D is glucosidically bound to the saccharide unit of the amino-saccharide. Endo- or exoglycosidase (EC group 3.2) are used as enzyme, and the reaction is carried out as a transglycosylation reaction. The equilibrium type reaction may also be chosen Non-limited examples of exoglycosidases are α-galactosidase, β-galactosidase, β-N-acetyl-glucosaminidase, β-N-acetyl-galactosaminidase, α-L-fucosidase, α-sialidase, α- or β-xylosidase, α-mannosidase or β-mannosidase.

The reaction conditions are chosen according to the reaction; some non-limiting examples are given below: The concentration of reactants are usually in the interval 0.05 M to above 1 M depending on the solubility of the reactants, the temperature is usually in the range 0° to 80° C. and the reaction is usually carried out in buffered water, pH 4–9; the pH and temperature are chosen according to e.g. the enzyme's properties, eventually an organic co-solvent can be used (1–99% of e.g. tetrahydrofurane or acetonitrile). The reaction is usually stopped when the maximum yield of amino-saccharide product has been obtained and the product is isolated with, for example, one or more of column chromatography (adsorbent for example ion-exchange material, Sephadex or silica), extraction, precipitation, crystallization and/or filtration techniques.

EXAMPLES

As a non-limiting specific example one can mention the production of thioetyl β-D-galactopyranosyl-(6-bensyl-2-amino-2-deoxy)-β-D-glucopyranoside produced via reaction between nitrophenyl β-D-galactopyranoside and thioetyl (6-bensyl-2-amino-2-deoxy)-β-D-glucopyranoside in e.g. sodium acetate buffer, pH 5, catalysed by β-galactosidase.

The product can be used either directly e.g. in biological/medical applications or can be used as a synthetic intermediate for further synthesis of higher oligosaccharides or other derivatives.

Synthesis of derivatives of Galβ1-3GlcNH$_2$ and Galβ1-4GlcNH$_2$ respectively (constituents of Lewis-blood group substances, such as Lewis-a, Lewis-x and sialylated structures): By using for example derivatised glycoside of glucosamine, such as e.g. structures IX or II, as acceptor dissolved in for example (1/1 V/V) tetrahydrofurane:sodium acetate buffer (pH 5.5, 0.05 M), Galβ-OPpNO$_2$-O as donor, and β-galactosidase as catalyst, structures of the types below can be obtained:

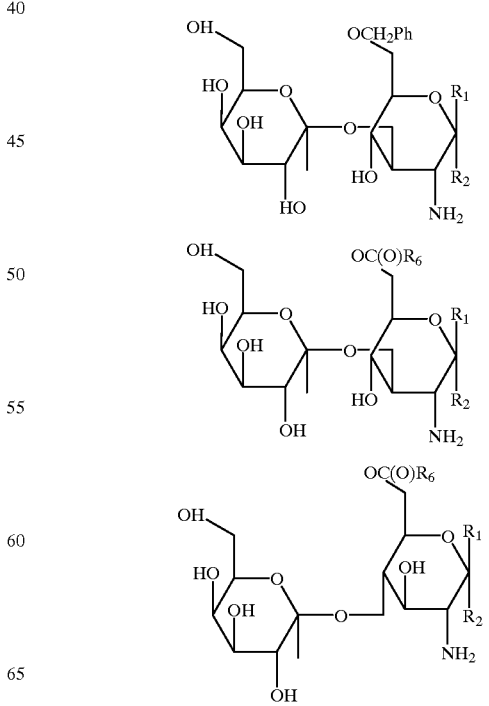

-continued

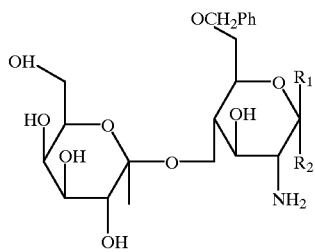

Such structures can be used directly in various applications, or can be used for further chemical or enzymatic synthesis. The galactosyl moiety can for example be modified with chemical or enzymatic methods (lipase or galactose oxidase, followed by chemical modification).leaving one free hydroxyl group in the glucosaminyl-moiety, which can be modified with for example a fucosyl group.

Similarly, by using an acceptor of the type below, the corresponding β-bound 3-O-protected Gal-GlcNH$_2$-derivative can be obtained.

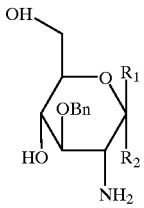

After protection of the free hydroxyl groups and the amino group in the product and deprotection of the 3-O-position can, for example, an α-bound L-fucosyl group can be introduced, which gives the modified Lewis-x structure, which can be, for example, sialylated to give e.g. NeuAcα2-3Galβ1-4(Fucα1-3)GlcNR$_2$—R. In an analogous way, one can produce regioisomers, such as Galβ1-3(Fucα1-4) GlcNR$_2$—R, and analogs/derivatives of Lewis-x, Lewis-a, and of sialylated Lewis-substances.

EXAMPLE 1

A non-limiting example of the application of the method according to the invention is the synthesis of Galβ1-3(6-O-Bn)GlcNH$_2$βSEt employing thioethyl (6-O-bensyl-2-amino-2-deoxy)-β-D-glucopyranosid, abbreviated (6-O-Bn) GlcNH$_2$βSEt, as acceptor and galactose or lactose or a galactoside, e.g. nitrophenyl α-D-galactopyranoside as glycosyl donor and β-galactosidase from ox testes as catalyst.

Other sources of β-galactosidase which gives the linkage may be used according to the invention. The reaction was carried out at room temperature with initial concentration of substrates typically in the range of 0.06 M to 0.3 M. The donor was used in excess over the acceptor. A crude ammonium sulfate precipitate of the enzyme was used in the reaction, which was carried out at pH 5 in 0.05 M sodium acetate buffer. The reaction was terminated by heat treatment for ca 5 minutes in a boiling water bath. The product was isolated by e.g. adjusting the pH to ca 10.5 (minimizing the charge on the amino group), extraction of the water phase with ethyl acetate, followed by butanol extraction, the butanol phase was evaporated and the residue dissolved in water and applied to an ion-exchanger (in this example a sulphopropyl group containing fast-flow ion-exchanger from Pharmacia). The fractions containing the product was evaporated and the product dried and analyzed by NMR.

Similarly, another 6-O-substituted product than the bensyl-substituted product and/or another type of 1-substituted derivative than the 1-thioethyl substituted product, can be obtained by instead of (6-OBn)GlcNH$_2$βSEt employing another 6-O- and/or 1-substituted acceptor as exemplified in the description.

Another non-limiting example is the synthesis of Fucα1-4(6-O-Bn)GlcNH$_2$βSEt using thioethyl (6-O-bensyl-2-amino-2-deoxy)-β-D-glucopyranoside, abbreviated (6-O-Bn)GlcNH$_2$βSEt, as acceptor and fucose or a fucopyranoside, e.g. nitrophenyl α-L-fucopyranoside as glycosyl donor and α-L-fucosidase from ox kidney as catalyst.

The reactions above can for example be carried out with ca 0.1 M concentrations of substrate and the isolation can be carried out by the use of an ion changer (e.g. sulphopropyl-containing material) and extraction of the water phase with a suitable solvent, e.g. butanol or ethylacetate.

The two substances above are of interest for example as inhibitors/modifiers of selectin-carbohydrate interactions in vivo such as in different inflammatory reactions e.g. septic chock, rheumatism and asthma, but also as inhibitors/modifiers of the up-regulation of IgE-synthesis in vivo (for example inhibition, modification of the FceRll-CR interaction, see e.g. Nature (1993), volume 366, page 41–48, and references therein, for an overview).

One of the advantages with the method according to the invention, is that the amino-disaccharide- or the amino-oligosaccharide product and derivatives thereof can be synthesized directly, and thus no modification of the amino-group is required after the glycosidase-catalysed reaction. Another advantage is that partially modified amino-sugar derivatives can be produced stereospecifically and under reaction specific conditions. Such derivatives can be used directly in various applications or as synthetic intermediates for further synthesis of higher oligosaccharides or other derivatives.

EXAMPLE 2

Synthesis of Galβ1-4(6-OBn)GlcNH$_2$βSEt. The synthesis of this compound is achieved similarly as above, but another source of enzyme which gives the β1-4 linked product, is employed, e.g. a yeast enzyme such as the one from Bullera singularis. In this case the reaction can be carried out as a fermentation with e.g. lactose as the glycosyl donor and with intact cells.

Similarly, another 6-O-substituted product than the bensyl-substituted product and/or another type of 1-substituted derivative than the 1-thioethyl substituted product, can be obtained by instead of (6-OBn)GlcNH$_2$βSEt employing another 6-O- and/or 1-substituted acceptor as exemplified in the description.

EXAMPLE 3

Synthesis of Galβ1-3GlcNH$_2$βSEt and Galβ1-3GalNH$_2$βSEt. See example 1, similar conditions and enzyme may be used, but instead GlcNH$_2$βSEt, or GalNH$_2$βSEt to obtain the latter product, is used as the acceptor. Here, extraction is less favorable for isolation, and instead ion-exchanger as above may be used followed by e.g. precipitation or a second chromatographic step.

EXAMPLE 4

Synthesis of Galβ1-4GlcNH$_2$βSEt. See example 3 for acceptor substrate and isolation. Here, the source of enzyme is used which gives the 1-4 linked product (cf. example 2).

If a microorganism like in example 2 above is used then a fermentation like in example 2 may be used.

EXAMPLE 5

Synthesis of Galβ1-3(6-OAll)GlcNH$_2$βSEt. This compound and other 6-substituted derivatives and other 1-substituted derivatives is obtained as in example 1 above, but instead of the 6-O-bensyl aminosaccharide the 6-O-allyl- or another 6-substituted derivative and/or another type of 1-substituted derivative is used as acceptor as mentioned in the description.

EXAMPLE 6

Synthesis of Galβ1-4(6-OAll)GlcNH$_2$βSEt. This compound and other 6-substituted derivatives and 1-substituted derivatives is obtained as in example 2 above employing a β-galactosidase which gives a 1-4-linked product, but instead of the 6-O-bensyl aminosaccharide the 6-O-allyl- or another 6-substituted derivative or another type of 1-substituted derivative is used as acceptor as mentioned in the description.

EXAMPLE 7

Synthesis of Galβ1-3(4-OBn)GlcNH$_2$βSEt. This compound and other 4-substituted derivatives and other 1-substituted derivatives is obtained as in example 1 above employing an enzyme which gives a 1-3-linked product, but instead of the 6-O-bensyl aminosaccharide the 4-O-bensyl- or another 4-substituted derivative and/or 1-substituted derivative is used as acceptor as mentioned in the description.

EXAMPLE 8

Synthesis of Galβ1-4(3-OBn)GlcNH$_2$βSEt. This compound and other 3-substituted derivatives is obtained as in example 2 above employing a β-galactosidase which gives a 1-4-linked product, but instead of the 6-O-bensyl aminosaccharide the 3-O-bensyl- or another 3-substituted derivative is used as acceptor.

EXAMPLE 9

Synthesis of Fucα1-4(6-OBn)GlcNH$_2$βSEt. The reaction was carried out at room temperature with initial concentration of substrates typically in the range 0.06 M to 0.1 M. A crude ammonium sulphate precipitate of the enzyme was used in the reaction, which was carried out at pH 5 in 0.05 M sodium acetate buffer. The reaction was terminated by heat treatment for ca 5 minutes in a boiling water-bath. The product was isolated by e.g. adjusting the pH to ca 10.5 (minimizing the charge on the amino-group), extraction of the water phase with ethyl acetate, followed by butanol extraction, the butanol phase was evaporated and the residue dissolved in water and applied to an ion-exchanger (in this example a sulphopropyl group containing fast-flow ion-exchanger from Pharmacia). The fractions containing the product was evaporated and the product dried and analyzed by NMR.

Similarly, another 6-O-substituted product than the bensyl-substituted product and/or another type of 1-substituted derivative than the 1-thioethyl substituted product, can be obtained by instead of (3-OBn)GlcNH$_2$βSEt employing another 6-O- and/or 1-substituted acceptor as exemplified in the description.

EXAMPLE 10

Synthesis of Fucα1-3(6-OBn)GlcNH$_2$βSEt. The synthesis of this compound is achieved similarly as above, but another source of enzyme, which gives the α1-3 linked product, is employed. Similarly, another 6-O-substituted product than the bensyl-substituted and/or another type of 1-substituted derivative than the 1-thioethyl substituted product, can be obtained by instead of (6-OBn)GlcNH$_2$βSEt employing another 6-O- and/or 1-substituted acceptor.

EXAMPLE 11

Synthesis of Fucα1-3(4-OBn)GlcNH$_2$βSEt. The synthesis of this compound is achieved similarly as above, but with (4-OBn)GlcNH$_2$βSEt as the acceptor. Similarly, another 4-O-substituted product than the bensyl-substituted and/or another type of 1-substituted derivative than the 1-thioethyl substituted product, can be obtained by instead of (4-OBn) GlcNH$_2$βSEt employing another 4-0- and/or 1-substituted acceptor.

EXAMPLE 12

Synthesis of Fucα1-4(3-OBn)GlcNH$_2$βSEt. The synthesis of this compound is achieved similarly as above, but with an enzyme which gives the α1-4-linked product and with (3-OBn)GlcNH$_2$βSEt as the acceptor. Similarly, another 3-0-substituted product than the bensyl-substituted and/or another type of 1-substituted derivative than the 1-thioethyl substituted product, can be obtained by instead of (3-OBn) GlcNH$_2$βSEt employing another 3-O- and/or 1-substituted acceptor.

EXAMPLE 13

Synthesis of compounds of the type GlcNAcβ1-3(6-OBn)GlcNH$_2$βSEt, GlcNAcβ1-4(6-OBn)GlcNH$_2$βSEt, GlcNAcβ1-4(3-OBn)GlcNH$_2$βSEt, GlcNAcβ1-3(4-OBn)GlcNH$_2$βSEt, GlcNAcβ1-3(6-OBn)GalNH$_2$βSEt, GlcNAcβ1-4(6-OBn)GalNH$_2$βSEt, GlcNAcβ1-4(3-OBn)GalNH$_2$βSEt and GlcNAcβ1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-β-D-glucosaminidase which gives the desired linkage, and by using as acceptor the proper one of (6-OBn)GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn)GalNH$_2$βSEt as well as other amino-saccharides of the above type substituted in the 1, 3, 4, or 6-positions with other type of groups, including saccharides, mentioned in the description. As glycosyl donor one can use GlcNAc, a glycoside thereof such as the F-β-glycoside or the nitrophenyl-β-glycoside.

EXAMPLE 14

Synthesis of compounds of the type GalNAcβ1-3(6-OBn)GlcNH$_2$βSEt, GalNAcβ1-4(6-OBn)GlcNH$_2$βSEt, GalNAcβ1-4(3-OBn)GlcNH$_2$βSEt, GalNAcβ1-3(4-OBn)GlcNH$_2$βSEt, GalNAcβ1-3(6-OBn)GalNH$_2$βSEt, GalNAcβ1-4(6-OBn)GalNH$_2$βSEt, GalNAcβ1-4(3-OBn)GalNH$_2$βSEt and GalNAcβ1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-β-D-galactosaminidase or another proper β-hexosaminidase which gives the desired linkage, and by using as acceptor the proper one of (6-OBn) GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn) GlcNH$_2$βSEt as well as other amino-saccharides of the above type substituted in the 1, 3, 4, or 6-positions with other type of groups, including saccharides, mentioned in the description. As glycosyl donor one can use GalNAc, a glycoside thereof such as the F-β-glycoside or the nitrophenyl-β-glycoside.

EXAMPLE 15

Synthesis of compounds of the type GalNAcα1-3(6-OBn)GlcNH$_2$βSEt, GalNAcα1-4(6-OBn)GlcNH$_2$βSEt, GalNAcα1-4(3-OBn)GlcNH$_2$βSEt, GalNAcα1-3(4-OBn)GlcNH$_2$βSEt, GalNAcα1-3(6-OBn)GalNH$_2$βSEt, GalNAcα1-4(6-OBn)GalNH$_2$βSEt, GalNAcα1-4(3-OBn)GalNH$_2$βSEt and GalNAcα1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-α-D-galactosaminidase or another proper α-hexosaminidase which gives the desired linkage, and by using as acceptor the proper one of (6-OBn)GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn)GlcNH$_2$βSEt as well as other amino-saccharides of the above type substituted in the 1, 3, 4, or 6-positions with other type of groups, including saccharides, mentioned in the description. As glycosyl donor one can use GalNAc, a glycoside thereof such as the F-β-glycoside or nitrophenyl-β-glycoside.

EXAMPLE 16

Synthesis of compounds of the type Manα1-3(6-OBn)GlcNH$_2$βSEt, Manα1-4(6-OBn)GlcNH$_2$βSEt, Manα1-4(3-OBn)GlcNH$_2$βSEt, Manα1-3(4-OBn)GlcNH$_2$βSEt, Manα1-3(6-OBn)GalNH$_2$βSEt, Manα1-4(6-OBn)GalNH$_2$βSEt, Manα1-4(3-OBn)GalNH$_2$βSEt and Manα1-3(4-OBn)GalNH$_2$βSEt as well as other amino-saccharides of the above type substituted in the 1, 3, 4, or 6-positions with other type of groups, including saccharides, mentioned in the description, are obtained by using α-D-mannosidase which gives the desired linkage, and by using as acceptor the proper one of (6-OBn)GlcNH$_2$βSEt, (3-OBn)GlcNH$_2$βSEt, (1-OBn)GlcNH$_2$βSEt, (6-OBn)GalNH$_2$βSEt, (3-OBn)GalNH$_2$βSEt and (4-OBn)GlcNH$_2$βSEt as well as other amino-saccharides of the above type substituted in the 1, 3, 4, or 6-positions with other type of groups, including saccharides, mentioned in the description. As glycosyl donor one can use mannose, a glycoside thereof such as the F-β-glycoside or the nitrophenyl-β-glycoside.

EXAMPLE 17

Synthesis of compounds of the type Glcβ1-3(6-OBn)GlcNH$_2$βSEt, Glcβ1-4(6-OBn)GlcNH$_2$βSEt, Glcβ1-4(3-OBn)GlcNH$_2$βSEt, Glcβ1-3(4-OBn)GlcNH$_2$βSEt, Glcβ1-3(6-OBn)GalNH$_2$βSEt, Glcβ1-4(6-OBn)GalNH$_2$βSEt, Glcβ1-4(3-OBn)GalNH$_2$βSEt and Glcβ1-3(4-OBn)GalNH$_2$βSEt as well as other amino-saccharides of the above type substituted in the 1, 3, 4, or 6-positions with other type of groups, including saccharides, mentioned in the description, are obtained by using β-D-glucosidase which gives the desired linkage and by using as acceptor the proper one of (6-OBn)GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn)GlcNH$_2$βSEt as well as other amino-saccharides of the above type substituted in the 1, 3, 4, or 6-positions with other type of groups, including saccharides, mentioned in the description. As glycosyl donor one can use mannose, a glycoside thereof such as the F-β-glycoside or the nitrophenyl-β-glycoside.

In examples 13, 14, 15, 16 and 17 above similar isolation procedures as in example 1 may be used.

Other saccharides than those mentioned above are obtained by using other glycosidases, including α- or β-xylosidases, α-sialidases and endoglycosidases, and other glycosyl donors as mentioned in the description.

A few non-limiting examples of the use of the invention for preparation of amino-deoxy-containing trisaccharides and higher saccharides in conjunction with glycosyltransferases are given below. The glycosyltransferases may be used in more or less isolated form, and may be of natural origin or may be obtained by any recombinant techniques. The glycosyl donors for the glycosyl transferases may be nucleotide sugars or modified nucleotide sugars or any type of glycosyl donor which can be used to promote the glycosyltranferase reaction. It is well known that glycosyltransferases can transfer modified and unnatural glycosyl units and di- tri- and higher oligosaccharides to their acceptors and this can also be used in the invention.

Moreover the glycosyl donors for the glycosyltransferase reactions can be produced either separately or in situ in the reaction vessel (by for instance multi-enzyme systems) and this does not limit the scope of the invention. Also, the glycosidase reaction can be either carried out separately or in the same reaction vessel as the glycosyltransferase reaction and this does not limit the scope of the invention. Moreover, either or both of the glycosidase and the glycosyltransferase can be used in soluble form or in immobilized form to any of the materials mentioned in the description.

EXAMPLE 18

Synthesis of NeuAcα2-3Galβ1-3GlcNH$_2$βSEt. Galβ1-3GlcNH$_2$βSEt is prepared as described above and used directly or after isolation as acceptor for a β-D-galactoside α2-3-sialyltransferase (e.g. EC 2.4.99.4) reaction with a suitable glycosyl donor such as CMP-NeuAc. Similarly, another 1-substituted product than the 1-thioethyl substituted product above can be obtained by instead of GlcNH$_2$βSEt employing another type of 1-substituted acceptor as exemplified in the description.

EXAMPLE 19

Synthesis of NeuAcα2-3Galβ1-4GlcNH$_2$βSEt, Galβ1-1GlcNH$_2$βSEt is prepared as described above and used directly or after isolation as acceptor for a β-D-galactoside α2-3-sialyltransferase.(e.g. EC 2.4.99.5) reaction with a suitable glycosyl donor such as CMP-NeuAc. Similarly, another 1-substituted product than the 1-thioethyl substituted product above, can be obtained by instead of GlcNH$_2$βSEt employing another type of 1-substituted acceptor as exemplified in the description.

EXAMPLE 20

Synthesis of NeuAcα2-3Galβ1-4(6-OBn)GlcNH$_2$βSEt. Galβ1-4(6-OBn)GlcNH$_2$βSEt is prepared as described above and used directly or after isolation as acceptor for a β-D-galactoside α2-3-sialytranferase (e.g. EC 2.4.99.5) reaction with a suitable glycosyl donor such as CMP-NeuAc. Similarly, another 6- and/or 1-substituted product than the 6-O-bensyl and 1-thioethyl substituted product above can be obtained by instead of 6-O-bensyl-GlcNH$_2$βSEt employing another type of 6- and/or 1-substituted acceptor as exemplified in the description.

EXAMPLE 21

Synthesis of NeuAcα2-3Galβ1-3(4-OBn)GlcNH$_2$βSEt. Galβ1-3(4-OBn)GlcNH$_2$βSEt is prepared as described above and used directly or after isolation as acceptor for a β-D-galactoside α2-3-sialyltransferase (e.g. EC 2.4.99.4) reaction with a suitable glycosyl donor such as CMP-NeuAc. Similarly, another 4- and/or 1-substituted product than the 4-O-bensyl and 1-thioethyl substituted product above, can be obtained by instead of 4-O-bensyl-GlcNH$_2$βSEt employing another type of 4- and/or 1-substituted acceptor as exemplified in the description.

EXAMPLE 22

Synthesis of NeuAcα2-3Galβ1-4(3-OBn)GlcNH$_2$βSEt. Galβ1-4(3-OBn)GlcNH$_2$βSEt is prepared as described above and used directly or after isolation as acceptor for a β-D-galactoside α2-3-sialyltransferase (e.g. EC 2.4.99.5) reaction with a suitable glycosyl donor such as CMP-NeuAc. Similarly, another 3- and/or 1-substituted product than the 3-O-bensyl and 1-thioethyl substituted product above, can be obtained by instead of 3-O-bensyl-GlcNH$_2$βSEt employing another type if 3- and/or 1-substituted acceptor as exemplified in the description.

EXAMPLE 23

Synthesis of NeuAcα2-6Galβ1-4GlcNH$_2$βSEt. Galβ1-4GlcNH$_2$βSEt is prepared as described above and used directly or after isolation as acceptor for a β-D-galactoside α2-6-sialyltransferase (e.g. EC 2.4.99.1) reaction with a suitable glycosyl donor such as CMP-NeuAc.

EXAMPLE 24

Synthesis of Galα1-3Galβ1-4GlcNH$_2$βSEt. Galβ1-4GlcNH$_2$βSEt is prepared as described above and used directly or after isolation as acceptor for a α1-3-D-galactosyltransferase (e.g. EC 2.4.1 151) reaction with a suitable glycosyl donor such as UDP-Gal.

EXAMPLE 25

Synthesis of Galβ1-4(Fucα1-3)GlcNH$_2$βSEt. Galβ1-4GlcNH$_2$βSEt is prepared as described above and used directly or after isolation as acceptor for a α1-3-fucosyltransferase (e.g. EC 2.4.1.152 or 65) reaction with a suitable glycosyl donor such as GDP-Fuc.

EXAMPLE 26

Synthesis of Fucα1-2Galβ1-4GlcNH$_2$βSEt. Galβ1-4GlcNH$_2$βSEt is prepared as described above and used directly or after isolation as acceptor for a α1-2-fucosyltransferase (e.g. EC 2.4.1.69) reaction with a suitable glycosyl donor such as GDP-Fuc.

EXAMPLE 27

Synthesis of Fucα1-2Galβ1-3GlcNH$_2$βSEt. Galβ1-3GlcNH$_2$βSEt is prepared as described above and used directly or after isolation as acceptor for a α1-2-fucosyltransferase (e.g. EC 2.4.1.69) reaction with a suitable glycosyl donor such as GDP-Fuc.

EXAMPLE 28

Synthesis of NeuAcα2-3Galβ1-3GalNH$_2$βSEt. Galβ1-3GalNH$_2$βSEt is prepared as described above and used directly or after isolation as acceptor for a α2-3-sialyltransferase (e.g. EC 2.4.99.4) reaction with a suitable glycosyl donor such as CMP-NeuAc.

EXAMPLE 29

Synthesis of NeuAcα2-3Galβ1-3(NeuAcα2-6)GalNH$_2$βSEt. NeuAcα2-3Galβ1-3GalNH$_2$βSEt is prepared as described above and used directly or after isolation as acceptor for a α2-6-sialyltransferase (e.g. EC 2.4.99.7) reaction with a suitable glycosyl donor such as CMP-NeuAc.

In the examples 23 to 29 above, other 1-substituted products than the 1-thioethyl substituted products above, can be obtained by instead of GlcNH$_2$βSEt employing another type of 1-substituted acceptor as exemplified in the description.

In the isolation of the compounds above, precipitation from water may be used if hydrophobic groups are present on the acceptors. Also extraction of the product from a solid crude mixture may be used with a suitable solvent e.g. MeOH. These techniques, precipitation and extraction are complementary to chromatography and a combination of one, two or all three of these techniques may be used for isolation.

Further variations and modifications of the foregoing will be apparent to those skilled in the art and such variations and modifications are attended to be encompassed by the claims that are appended hereto.

Swedish Priority Application 9301677-2 filed on May 17, 1993 is relied on and incorporated by reference.

U.S. Pat. No. 5,246,840; U.S. Pat. No. 4,918,009; U.S. Pat. No. 4,415,665; U.S. patent application Ser. No. 07/834,575, filed on Feb. 18, 1992, now U.S. Pat. No. 5,372,937; and U.S. patent application Ser. No. 07/940,866, filed on Oct. 29, 1992, now abandoned are incorporated by reference in their entirety (especially for their teachings concerning acceptor substances, donor substances, and enzymes). WO 93/03168 (PCT/SE92/00541) is incorporated by reference in its entirety (especially for its teachings concerning acceptor substances, donor substances, and enzymes).

I claim:

1. An amino-deoxy di- or olisosaccharide compound which is selected from the group consisting of Galβ1-3(6-O-Bn)GlcNH$_2$βSEt, Fucα1-4 (6-O-Bn)GlcNH$_2$βSEt, Gal1-4(6-OBn)GlcNH$_2$SEt, Galβ1-3GlcNH$_2$βSEt, Galβ1-3GalNH$_2$βSEt, Galβ1-4GlcNH$_2$βSEt, Galβ1-3(6-OAll)GlcNH$_2$βSEt, Galβ1-4(6-OAll)GlcNH$_2$βSEt, Galβ1-3(4-OBn)GlcNH$_2$βSEt, Galβ1-4(3-OBn)GlcNH$_2$βSEt, Fucα1-4 (6-OBn)GlcNH$_2$βSEt, Fucα1-3(6-OBn)GlcNH$_2$βSEt, Fucα1-3(4-OBn)GlcNH$_2$βSEt, Fucα1-4(3-OBn)GlcNH$_2$βSEt, GlcNAcβ1-3(6-OBn)GlcNH$_2$βSEt, GlcNAcβ1-4(6-OBn)GlcNH$_2$βSEt, GlcNAcβ1-4(3-OBn)GlcNH$_2$βSEt, GlcNAcβ1-3(4-OBn)GlcNH$_2$βSEt, GlcNacβ1-3(6-OBn)GalNH$_2$βSEt, GlcNacβ1-4(6-OBn)GalNH$_2$βSEt, GlcNacβ1-4(3-OBn)GalNH$_2$βSEt, GlcNAcβ1-3(4-OBn)GalNH$_2$βSEt, GalNAcβ1-3(6-OBn)GlcNH$_2$βSEt, GalNAcβ1-4(6-OBn)GlcNH$_2$βSEt, GalNAcβ1-4(3-OBn)GlcNH$_2$βSEt, GalNAcβ1-3(4-OBn)GlcNH$_2$βSEt, GalNAcβ1-3(6-OBn)GalNH$_2$βSEt, GalNAcβ1-4(6-OBn)GalNH$_2$βSEt, GalNAcβ1-4(3-OBn)GalNH$_2$βSEt, GalNAcβ1-3(4-OBn)GalNH$_2$βSEt, GalNAcα1-3(6-OBn)GlcNH$_2$βSEt, GalNAcα1-4(6-OBn)GlcNH$_2$βSEt, GalNAcα1-4(3-OBn)GlcNH$_2$βSEt, GalNAcα1-3(6-OBn)GalNH$_2$βSEt, GalNAcα1-4(6-OBn)GalNH$_2$βSEt, GalNAcα1-4(3-OBn)GalNH$_2$βSEt, GalNAcα1-3(4-OBn)GalNH$_2$βSEt, Manα1-3(6-OBn)GlcNH$_2$βSEt, Manα1-4(6-OBn)GlcNH$_2$βSEt, Manα1-4(3-OBn)GlcNH$_2$βSEt, Manα1-3(4-OBn)GlcNH$_2$βSEt, Manα1-3(6-OBn)GalNH$_2$βSEt, Manα1-4(6-OBn)GalNH$_2$βSEt, Manα1-4(3-OBn)GalNH$_2$βSEt, Manα1-3(4-OBn)GalNH$_2$βSEt, Glcβ1-3(6-OBn)GlcNH$_2$βSEt, Glcβ1-4(6-OBn)GlcNH$_2$βSEt, Glcβ1-4(3-OBn)GlcNH$_2$βSEt, Glcβ1-3(4-OBn)

GlcNH$_2$βSEt, Glcβ1-3(6-OBn)GalNH$_2$βSEt, Glcβ1-4(6-OBn)GalNH$_2$βSEt, Glcβ1-4(3-OBn)GalNH$_2$βSEt, Glcβ1-3(4-OBn)GalNH$_2$βSEt, NeuAcα2-3Galβ1-3GlcNH$_2$βSEt, NeuAcα2-3Galβ1-4GlcNH$_2$βSEt, NeuAcα2-3Galβ1-4(6-OBn)GlcNH$_2$βSEt, NeuAcα2-3Galβ1-3(4-OBn)GlcNH$_2$βSEt, NeuAcα2-3Galβ1-4(3-OBn)GlcNH$_2$βSEt, NeuAcα2-6Gal1-4GlcNH$_2$βSEt, Galα1-3Galβ1-4GlcNH$_2$βSEt, Galβ1-4(Fucα1-3)GlcNH$_2$βSEt, Fucα1-2Galβ1-4GlcNH$_2$βSEt, Fucα1-2Galβ1-3GlcNH$_2$βSEt, NeuAcα2-3Galβ1-3GalNH$_2$βSEt, and NeuAcα2-3Galβ1-3(NeuAcα2-6)GalNH$_2$βSEt.

* * * * *